United States Patent [19]

Laforest

[11] 4,219,663
[45] Aug. 26, 1980

[54] (2,3-DICHLORO-4-CARBOXY)PHENOXY ACETIC ACID AND ESTERS THEREOF

[75] Inventor: Jacqueline S. Laforest, Vincennes, France

[73] Assignee: SmithKline Corporation, Philadelphia, Pa.

[21] Appl. No.: 920,046

[22] Filed: Jun. 28, 1978

Related U.S. Application Data

[62] Division of Ser. No. 834,209, Sep. 19, 1977, abandoned.

[51] Int. Cl.$^2$ ............................................. C07C 63/14
[52] U.S. Cl. ....................................... 560/62; 549/70; 562/472
[58] Field of Search ........................... 560/62; 562/472

[56] References Cited
PUBLICATIONS

P. S. Tarbell et al., JACS 64: 1066–1070, 607–612, 1942.
Chem. Abstr. 41:3905e.

*Primary Examiner*—Paul J. Killos
*Attorney, Agent, or Firm*—Richard D. Foggio

[57] ABSTRACT

2,3-Dichloro-4-(2-thenoyl)phenoxyacetic acid (tienilic acid) is prepared by reacting (2,3-dichloro-4-carboxy)-phenoxyacetic acid with thiophene in the presence of a dehydration agent. The (2,3-dichloro-4-carboxy)-phenoxyacetic acid is a novel compound.

3 Claims, No Drawings

(2,3-DICHLORO-4-CARBOXY)PHENOXY ACETIC ACID AND ESTERS THEREOF

This is a division of application Ser. No. 834,209 filed Sept. 19, 1977, now abandoned.

The present invention is concerned with a new process for the preparation of 2,3-dichloro-4-(2-thenoyl) phenoxyacetic acid (tienilic acid), diuretic and uricosuric agent used in human therapy.

In contrast to the synthesis described in French Patent 2,068,403 carbonyl function is no longer created by the reaction of a derivative of 2-thiophenecarboxylic acid on a benzene base (2,3-dichloroanisole or 2,3-dichlorophenoxyacetic acid), in the presence of a Lewis catalyst.

According to this invention the ketone function is created by alkylation of thiophene by a compound of the formula:

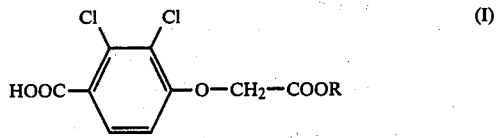

in which R represents a hydrogen atom or an alkyl group, in the presence of a dehydration agent such as polyphosphoric acid or trifluoroacetic anhydride and preferably with a third solvent which is, for example, benzene, methylene chloride or dichloroethane. The reaction is carried out until completion, and conveniently for from about 1-8 hours. It is possible to use as another dehydration agent the result of the action of phosphoric anhydride on methane sulfonic acid, as described in J. Org. Chem. 38 4071 (1973). Nevertheless the yields of the reaction are lower in the latter case.

Alternatively, the compound of formula I wherein R represents an alkyl group is converted to the corresponding acid chloride by reaction with thionyl chloride and then condensed with thiophene in the presence of stannic chloride and in a solvent such as 1,2-dichloroethane.

In the above formula I, R preferably represents an alkyl group of $C_1$-$C_4$ and more particularly an ethyl group.

The compound of formula I is prepared from 2,3-dichloroanisole by carrying out, for example, the following reactions:

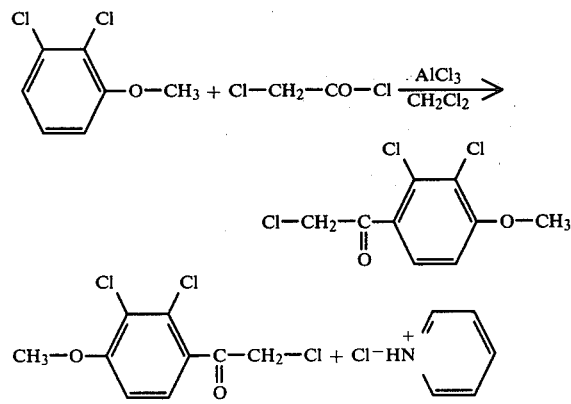

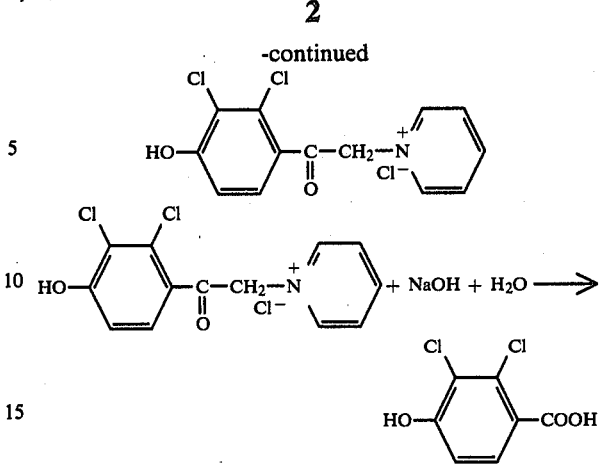

From (2,3-dichloro-4-hydroxy) benzoic acid one obtains (2,3-dichloro-4-carboxy) phenoxyacetic acid by the action of monochloracetic acid in the presence of sodium hydroxide or also by the action of ethyl monochloracetate followed by hydrolysis. It is possible to transform (2,3-dichloro-4-carboxy) phenoxyacetic acid into its ethyl ester, whose better solubility in an organic medium is significant, for example by monoesterification.

The compound described above, namely (2,3-dichloro-4-carboxy) phenoxyacetic acid, in addition to utility as an intermediate has diuretic and uricosuric activity as demonstrated in standard pharmacological procedures summarized as follows.

DIURETIC AND URICOSURIC ACTIVITY

The diuretic and uricosuric activity of (2,3-dichloro-4-carboxy)phenoxyacetic acid is determined by intravenous administration to the phosphate-mannitol infused mongrel dog. From renal clearance studies the effect of the test compound upon kidney function is determined by measurement of effective renal plasma flow, glomerular filtration rate and filtration fraction. Urine volume, pH, electrolyte and uric acid excretion are also determined. In this study, (2,3-dichloro-4-carboxy) phenoxyacetic acid at a dose of 60 mg/kg i.v. increased sodium and potassium excretion and increased uric acid filtered by 116%.

The following example illustrates the invention without nevertheless limiting its scope.

EXAMPLE

(A) Preparation of (2,3-dichloro-b 4-methoxyphenyl) chloromethyl ketone 40 g. of aluminum chloride is added in small portions to a solution, kept at 0° C., of 53 g. of 2,3-dichloroanisole and 37 g. of chloracetyl chloride in 400 ml. of methylene chloride. After 2 hours at 0° C., the mixture is kept for 12 hours at 25° C. and then poured over a mixture of ice and concentrated hydrochloric acid. The organic phase is decanted and the aqueous phase is once again extracted with chloroform. The residue obtained after evaporating the organic solvents is recrystallized in a mixture of benzene and petroleum ether (1/1) to give in 80% yield, the ketone which melts at 90° C.

(B) Preparation of N-[(2,3-dichloro-4-hydroxyphenyl) carbonylmethyl] pyridinium chloride A mixture of 231 g. of pyridine hydrochloride and 77 g. of the previously obtained ketone is kept for 10 minutes at 170° C. and then cooled to 100° C.; then 3 volumes of ice water and 10 ml. of 1 N aqueous solution of hydrochloric acid is added.

The precipitate is isolated and then washed with boiling methanol to obtain in 75% yield, the pyridine derivative which melts higher than 250° C.

(C) Preparation of (2,3-dichloro-4-hydroxy) benzoic acid 49.6 g. of the preceding compound is suspended in 400 ml. of water containing 20 g. of sodium hydroxide and the mixture is kept at the reflux temperature until the solid has completely disappeared, i.e., about 4 hours. The solution is acidified by adding concentrated hydrochloric acid. The precipitate formed is separated out and recrystallized from dichloroethane to give in 95% yield, the acid which melts at 205° C.

(D) (2,3-Dichloro-4-carboxy) phenoxyacetic acid is then prepared by the action of sodium monochloracetic on the phenol compound prepared in (C), in the presence of sodium hydroxide in aqueous or alcoholic solution, or also by the action of ethylmonochloracetate on the compound prepared in (C) in alcohol solution, followed by hydrolysis in a basic aqueous medium.

Method 1

17 g. of (2,3-dichloro-4-hydroxy) benzoic acid is added to 100 ml. of a 3 N aqueous solution of sodium hydroxide, followed by the addition of 9.45 g. of monochloracetic acid. After 2 hours of reflux, 5 g. of sodium hydroxide and 4.7 g. of monochloracetic acid is added once again and the reflux is extended for 2 hours.

The aqueous solution is then acidified and the precipitate is filtered and recrystallized in a dioxane/water mixture (50/50) to give the acid product which melts at more than 250° C., with 70% yield.

Method 2

4.8 g. of (2,3-dichloro-4-hydroxy) benzoic acid is heated for 1 hour at the reflux temperature in 50 ml. of ethyl alcohol containing 2.65 g. of potassium hydroxide and 3.9 g. of potassium iodide. Then 5.9 g. of ethyl monochloracetate is added and the mixture is kept at the reflux temperature until it becomes neutral. 50 ml. of water and 5 g. of potassium hydroxide is then added and the mixture refluxed for another 1½ hours. The reaction mixture is cooled, poured into water, and acidified with hydrochloric acid, separating the precipitated diacid (yield 75%).

Ethyl (2,3-dichloro-4-carboxy) phenoxyacetate is obtained by monoesterification of the diacid. Thus 20 g. of the diacid is dissolved in 250 ml. of benzene and 250 ml. of ethyl alcohol and 1.2 ml. of concentrated sulfuric acid is added. The solution is kept at the reflux temperature for 3 hours. After neutralization by adding sodium bicarbonate, the solvents are evaporated and the residue is dissolved in an aqueous solution of sodium carbonate. The aqueous phase is then acidified and the precipitate is filtered and recrystallized from 1,2-dichloroethane by filtering hot; the precipitate obtained melts at 166° C. (yield 50%).

(E) Preparation of tienilic acid

Method 1

5.12 g. of Ethyl(2,3-dichloro-4-carboxy)phenoxyacetic and 1.68 g. of thiophene are added to a mixture of 40 g. of polyphosphoric acid and 200 ml. of benzene, while vigourously agitating. The reaction mixture is kept for 10 hours at the reflux temperature of benzene and then is poured into 2 volumes of water. The benzene phase is decanted and the aqueous phase is extracted with ether. The organic phases are washed with an aqueous solution of sodium hydroxide, dried, and the solvents evaporated. 1.2 g. of Ethyl 2,3-dichloro-4-(2-thenoyl) phenoxyacetic is isolated, which is hydrolyzed by the action of potassium hydroxide in ethyl alcohol at the reflux temperature in order to obtain tienilic acid with a yield of 90%.

During this reaction it is also possible to use as a olvent methylene chloride or 1,2-dichloroethane. Also, thiophene may be added in portions during the course of heating.

Furthermore, it is also possible to use the same procedural method to acylate the (2,3-dichloro-4-carboxy) phenoxyacetic acid.

Method 2

6 g. of Ethyl (2,3-dichloro-4-carboxy) phenoxyacetate and 30 ml. of thionyl chloride are heated 3 hours at about 80° C. Benzene is added and the liquid distilled under reduced pressure.

The crude product (2,3-dichloro-4-carbethoxymethoxy) benzoylchloride remains as a solid, m.p. 80° C.

2.8 g. of Thiophene and 8.5 g. of the acid chloride obtained above are dissolved in 100 ml. of 1,2-dichloroethane. At about 0° C., 3.2 ml. of stannic chloride introduced in the solution. The mixture is slowly heated to 60° C. and this temperature is maintained 2 hours. Ice water and hydrochloric acid are poured in, the organic phase decanted and the solvent evaporated. The crude product is recrystallized in a mixture of ethanol/water (75/25) to give 6 g. of the pure ester.

What is claimed is:

1. A chemical compound having the formula:

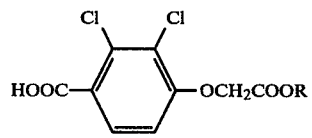

in which R represents hydrogen or lower alkyl of from one to four carbon atoms.

2. The chemical compound of claim 1 wherein R is hydrogen.

3. The chemical compound of claim 1 wherein R is ethyl.

* * * * *

UNITED STATES PATENT AND TRADEMARK OFFICE
CERTIFICATE OF CORRECTION

PATENT NO. : 4,219,663

DATED : August 26, 1980

INVENTOR(S) : Jacqueline S. Laforest

It is certified that error appears in the above-identified patent and that said Letters Patent are hereby corrected as shown below:

On the first page of the patent, in the left-hand column, item [73] should read:

[73] Assignee: Albert Rolland, S. A.
Chilly-Mazarin, France

Signed and Sealed this

Twenty-fifth Day of November 1980

[SEAL]

Attest:

SIDNEY A. DIAMOND

Attesting Officer

Commissioner of Patents and Trademarks